(12) United States Patent
Brim

(10) Patent No.: US 6,190,341 B1
(45) Date of Patent: Feb. 20, 2001

(54) PROTECTIVE KNEE BRACE

(76) Inventor: Evander Brim, 21203 E. Belleview Pl., Aurora, CO (US) 80015

( * ) Notice: Under 35 U.S.C. 154(b), the term of this patent shall be extended for 0 days.

(21) Appl. No.: 09/591,067

(22) Filed: Jun. 9, 2000

(51) Int. Cl.$^7$ ........................................ A61F 5/00
(52) U.S. Cl. .................................. 602/5; 602/16; 602/23; 602/26
(58) Field of Search .................................... 128/877, 878, 128/879, 882; 602/5, 16, 23, 26

(56) References Cited

U.S. PATENT DOCUMENTS

| | | | | |
|---|---|---|---|---|
| 5,009,223 | * | 4/1991 | Defonce | 602/16 |
| 5,107,824 | * | 4/1992 | Rogers | 606/26 |
| 5,286,250 | * | 2/1994 | Meyers | 602/26 |
| 5,330,418 | * | 7/1994 | Townsend | 602/26 |
| 5,344,390 | * | 9/1994 | Motloch | 602/26 |
| 5,611,774 | * | 3/1997 | Postelmans | 602/26 |

* cited by examiner

*Primary Examiner*—Michael A. Brown

(57) ABSTRACT

A protective knee brace for preventing hyperextension to a user's knee upon frontal impact thereto. The protective knee brace includes an upper brace member having a laterally curved shell having an outwardly protruding front portion near a bottom thereof and further having side portions with end portions extending downwardly below the bottom of the upper brace member, and further having a padded member lining a back side of the curved shell; and also includes a lower brace member having a laterally curved shell having an outwardly protruding front portion near a top thereof and being overlapped by the upper brace member, and further having a padded member lining the back side of the curved shell; and further includes tracks disposed in the end portions of the upper brace member; and also includes roller members securely mounted to the lower brace member and being movably disposed in the tracks; and further includes stop members securely attached to the lower brace member for limiting movement of the upper brace member; and also includes fastening members for fastening the brace members about the user's leg.

15 Claims, 3 Drawing Sheets

PROTECTIVE KNEE BRACE

BACKGROUND OF THE INVENTION

1. Field of the Invention

The present invention relates to a protective knee device to prevent hyperextension to a user's knee and more particularly pertains to a new protective knee brace for preventing hyperextension to a user's knee upon frontal impact thereto.

2. Description of the Prior Art

The use of protective knee device to prevent hyperextension to a user's knee is known in the prior art. More specifically, protective knee device to prevent hyperextension to a user's knee heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 3,194,233; U.S. Pat. No. 3,902,482; U.S. Pat. No. 3,528,412; U.S. Pat. No. 3,799,158; U.S. Pat. No. Des. 255,385; and U.S. Pat. No. 4,428,639.

While these devices fulfill their respective, particular objectives and requirements, the aforementioned patents do not disclose a new protective knee brace. The inventive device includes an upper brace member having a laterally curved shell having an outwardly protruding front portion near a bottom thereof and further having side portions with end portions extending downwardly below the bottom of the upper brace member, and further having a padded member lining a back side of the curved shell; and also includes a lower brace member having a laterally curved shell having an outwardly protruding front portion near a top thereof and being overlapped by the upper brace member, and further having a padded member lining the back side of the curved shell; and further includes tracks disposed in the end portions of the upper brace member; and also includes roller members securely mounted to the lower brace member and being movably disposed in the tracks; and further includes stop members securely attached to the lower brace member for limiting movement of the upper brace member; and also includes fastening members for fastening the brace members about the user's leg.

In these respects, the protective knee brace according to the present invention substantially departs from the conventional concepts and designs of the prior art, and in so doing provides an apparatus primarily developed for the purpose of preventing hyperextension to a user's knee upon frontal impact thereto.

SUMMARY OF THE INVENTION

In view of foregoing disadvantages inherent in the known types of protective knee device to prevent hyperextension to a user's knee now present in the prior art, the present invention provides a new protective knee brace construction wherein the same can be utilized for preventing hyperextension to a user's knee upon frontal impact thereto.

The general purpose of the present invention, which will be described subsequently in greater detail, is to provide a new protective knee brace which has many of the advantages of the protective knee device to prevent hyperextension to a user's knee mentioned heretofore and many novel features that result in a new protective knee brace which is not anticipated, rendered obvious, suggested, or even implied by any of the prior art protective knee device to prevent hyperextension to a user's knee, either alone or in any combination thereof.

To attain this, the present invention generally comprises an upper brace member having a laterally curved shell having an outwardly protruding front portion near a bottom thereof and further having side portions with end portions extending downwardly below the bottom of the upper brace member, and further having a padded member lining a back side of the curved shell; and also includes a lower brace member having a laterally curved shell having an outwardly protruding front portion near a top thereof and being overlapped by the upper brace member, and further having a padded member lining the back side of the curved shell; and further includes tracks disposed in the end portions of the upper brace member; and also includes roller members securely mounted to the lower brace member and being movably disposed in the tracks; and further includes stop members securely attached to the lower brace member for limiting movement of the upper brace member; and also includes fastening members for fastening the brace members about the user's leg.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new protective knee brace which has many of the advantages of the protective knee device to prevent hyperextension to a user's knee mentioned heretofore and many novel features that result in a new protective knee brace which is not anticipated, rendered obvious, suggested, or even implied by any of the prior art protective knee device to prevent hyperextension to a user's knee, either alone or in any combination thereof.

It is another object of the present invention to provide a new protective knee brace which may be easily and efficiently manufactured and marketed.

It is a further object of the present invention to provide a new protective knee brace which is of a durable and reliable construction.

An even further object of the present invention is to provide a new protective knee brace which is susceptible of a low cost of manufacture with regard to both materials and labor, and which accordingly is then susceptible of low prices of sale to the consuming public, thereby making such protective knee brace economically available to the buying public.

Still yet another object of the present invention is to provide a new protective knee brace which provides in the apparatuses and methods of the prior art some of the advantages thereof, while simultaneously overcoming some of the disadvantages normally associated therewith.

Still another object of the present invention is to provide a new protective knee brace for preventing hyperextension to a user's knee upon frontal impact thereto.

Yet another object of the present invention is to provide a new protective knee brace which includes an upper brace member having a laterally curved shell having an outwardly protruding front portion near a bottom thereof and further having side portions with end portions extending downwardly below the bottom of the upper brace member, and further having a padded member lining a back side of the curved shell; and also includes a lower brace member having a laterally curved shell having an outwardly protruding front portion near a top thereof and being overlapped by the upper brace member, and further having a padded member lining the back side of the curved shell; and further includes tracks disposed in the end portions of the upper brace member; and also includes roller members securely mounted to the lower brace member and being movably disposed in the tracks; and further includes stop members securely attached to the lower brace member for limiting movement of the upper brace member; and also includes fastening members for fastening the brace members about the user's leg.

Still yet another object of the present invention is to provide a new protective knee brace that reduces possible injury to the user's knee.

Even still another object of the present invention is to provide a new protective knee brace that is convenient and easy to wear and doesn't limit the user's mobility.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
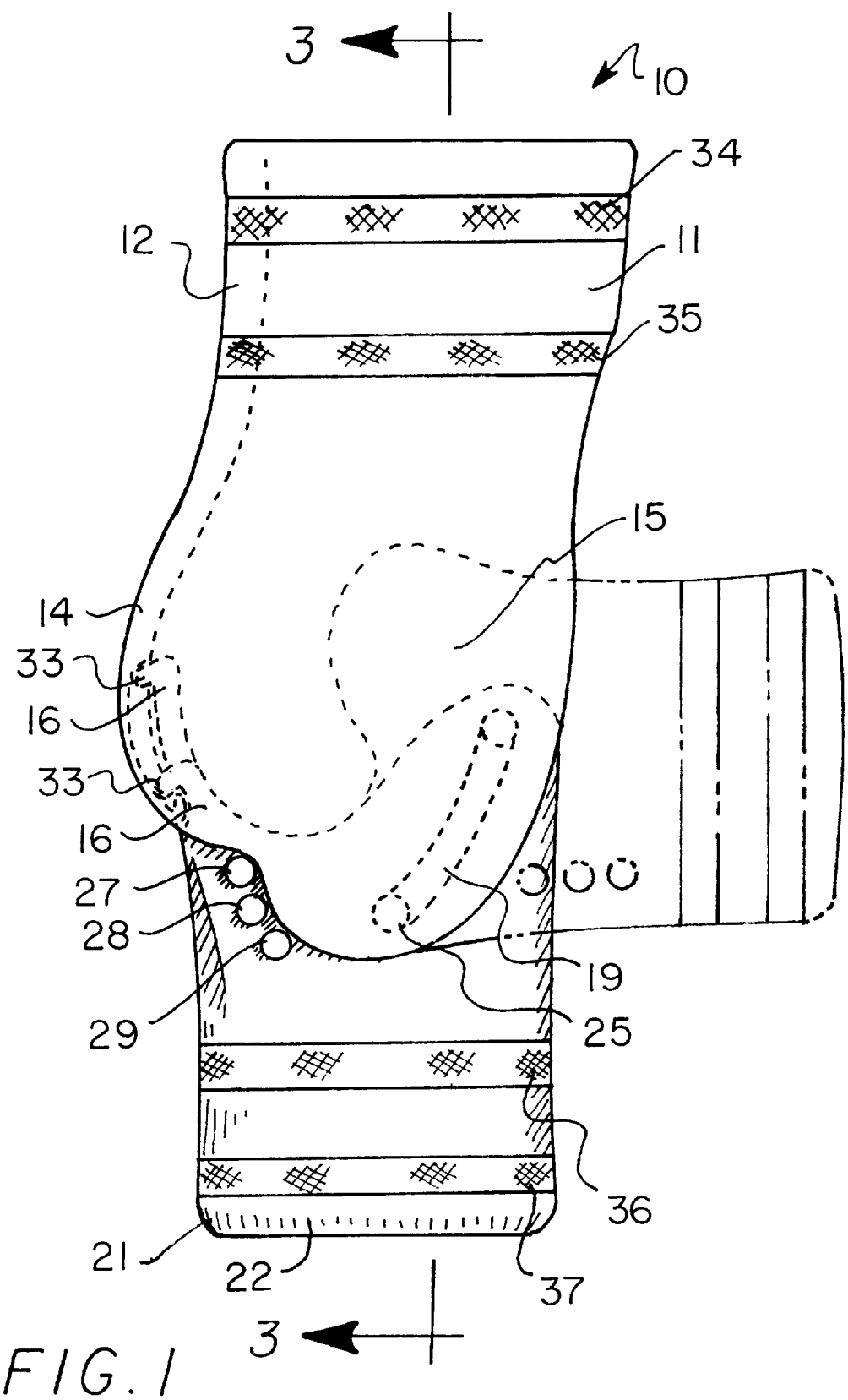
FIG. 1 is a side elevational view of a new protective knee brace according to the present invention.
Figure 2:
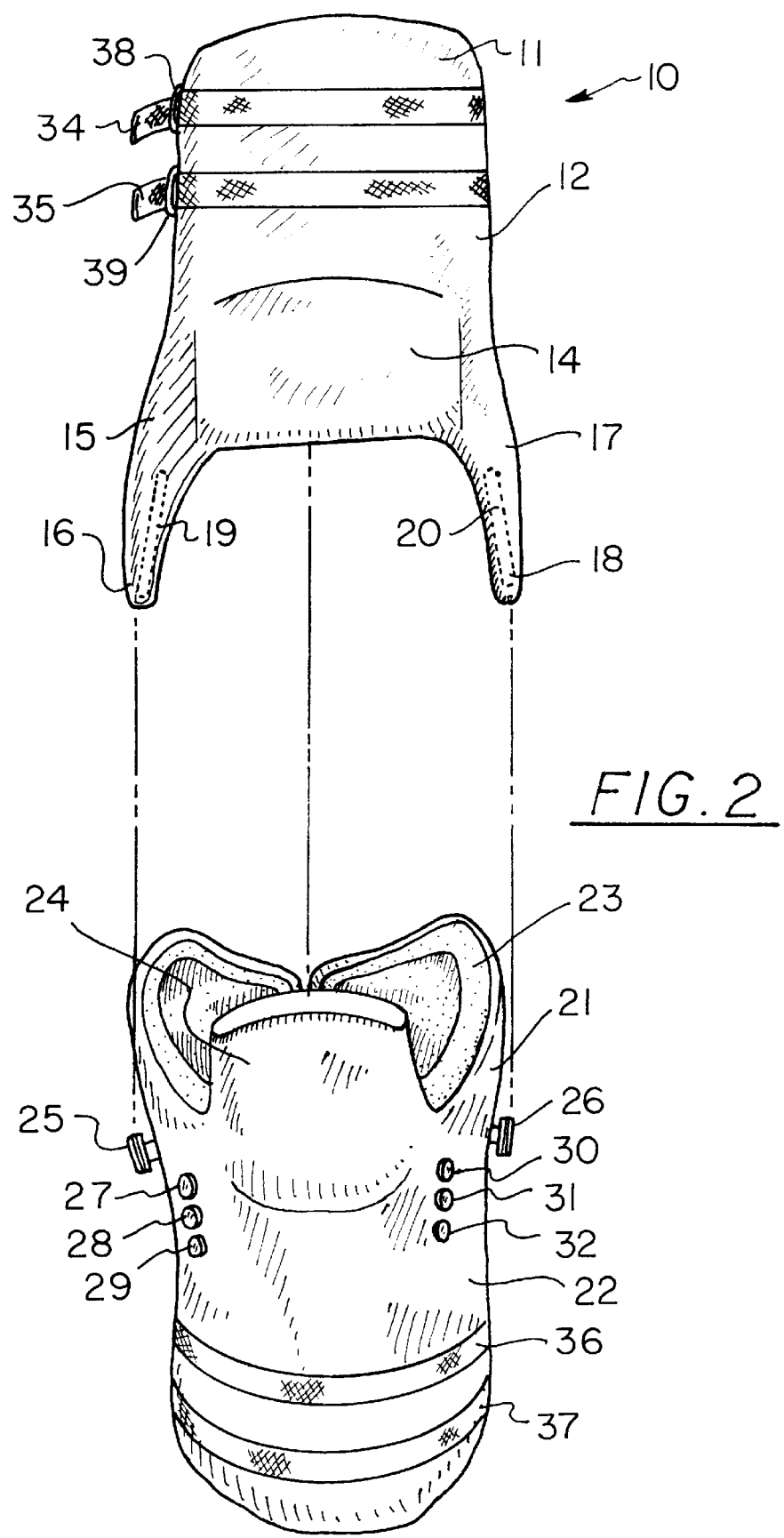
FIG. 2 is an exploded front elevational view of the present invention.
Figure 3:
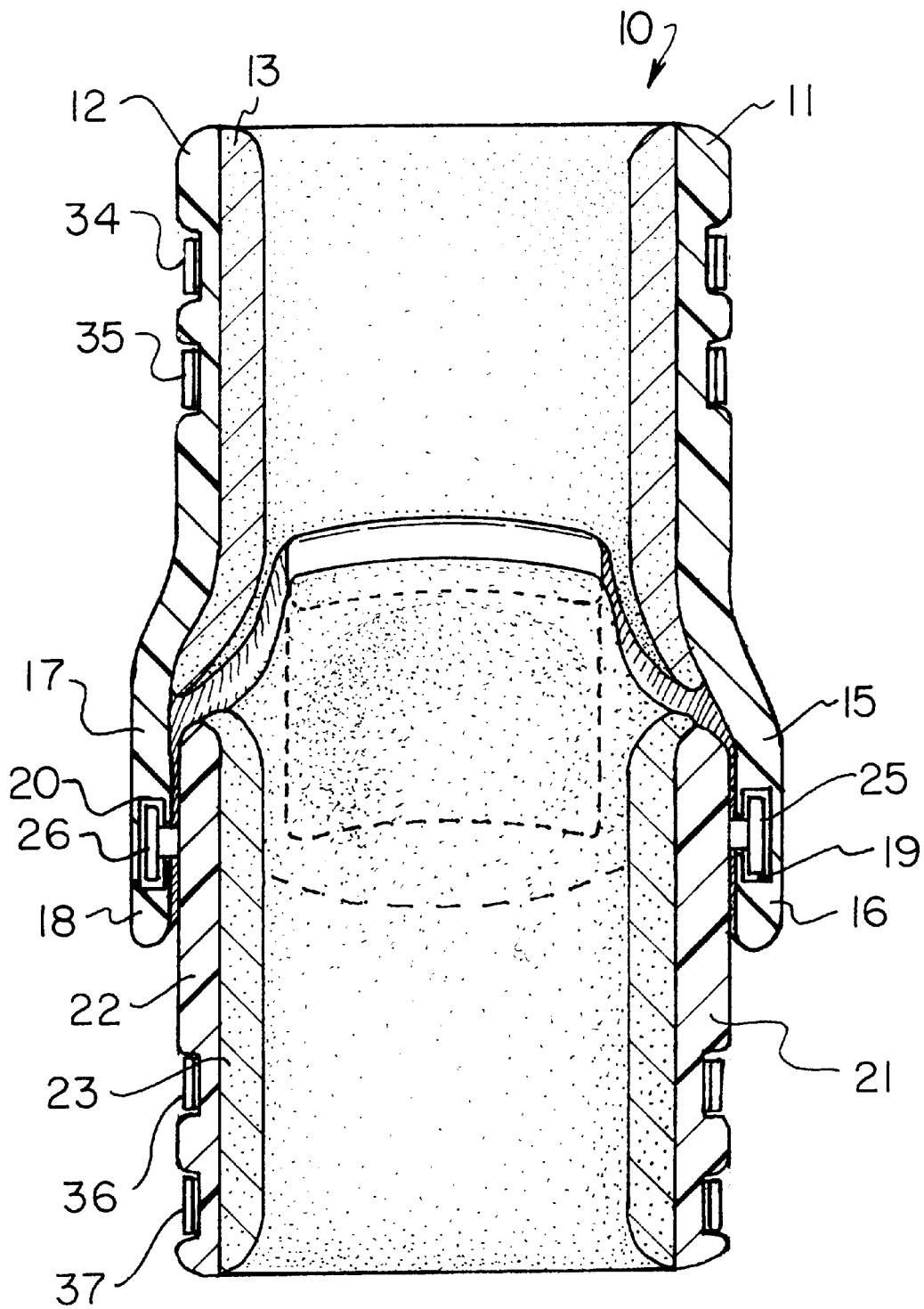
FIG. 3 is a cross-sectional view of the present invention.

With reference now to the drawings, and in particular to FIGS. 1 through 3 thereof, a new protective knee brace embodying the principles and concepts of the present invention and generally designated by the reference numeral 10 will be described.

As best illustrated in FIGS. 1 through 3, the protective knee brace 10 generally comprises an upper brace member 11 having a laterally curved shell 12 and a padded member 13 securely and conventionally lining a back side of the curved shell 12. The upper brace member 11 is adapted to fit about a user's leg above and including the knee. The curved shell 12 of the upper brace member 11 includes a front portion having an outwardly and forwardly protruding portion 14 near a bottom thereof, and includes first and second side portions 15,17 each of which has an end portion 16,18 which extends downwardly below the bottom of the front portion thereof. The padded member 13 is essentially thinsulate fabric with the curved shell 12 being essentially a high-impact material.

The protective knee brace 10 also includes a lower brace member 21 having a laterally curved shell 22 and a padded member 23 securely and conventionally lining a back side of the curved shell 22. The lower brace member 21 is adapted to fit about a user leg below and including the knee. The upper brace member 11 has a lower portion which overlaps an upper portion of the lower brace member 21. The curved shell 22 of the lower brace member 21 includes a front portion having an outwardly and forwardly protruding portion 24 near a top thereof with the outwardly and forwardly protruding portion 24 of the lower brace member 21 being adapted to receive the user's knee. The outwardly and forwardly protruding portion 14 of the upper brace member 1 is adapted to receive the outwardly and forwardly protruding portion 24 of the lower brace member 21. The end portions 16,18 of the side portions 15,17 of the upper brace member 11 and the outwardly protruding portion 14 of the upper brace member 11 overlaps the upper portion of the lower brace member 21 with the padded member 23 being essentially a thinsulate fabric and the curved shell 22 being essentially a high-impact material.

The protective knee brace 10 further includes a plurality of fastening members 34–39 a first ones 34,35,38,39 of which are securely and conventionally attached or sewn to the upper brace member 11 for securing the upper brace member 11 about the user's leg, and second ones 38,39 of which are securely and conventionally attached or sewn to the lower brace member 21 for securing the lower brace member 21 about the user's leg. Each of the fastening members includes a strap 34–37 being securely attached or sewn to a respective brace member 11,21 and being adapted to wrap about a user's leg, and also includes a buckle 38,39 also being securely and conventionally attached to a respective brace member 11,21 and being adapted to receive an end portion of a respective strap 34–37. The first ones of the fastening members include a pair of the fastening members being securely attached near a top of the upper brace member 11. The second ones of the fastening members include a pair of the fastening members being securely attached near the bottom of the lower brace member 21.

A plurality of tracks 19,20 are disposed in the lower portion of the upper brace member 11. The tracks 19,20 include a first one of the tracks 19 which is disposed in and extends along one of the end portions 16 of the curved shell 12 of the upper brace member 11, and also include a second one of the tracks 20 which is disposed in and extends along the other of the end portions 18 of the curved shell 12 of the upper brace member 11.

A plurality roller members 25,26 are securely and conventionally mounted to an exterior of the lower brace member 21 to either side thereof and being adapted to be movably received in the tracks 19,20. The roller members 25,26 are essentially roller bearings which extend outwardly of the lower brace member 21.

A plurality of stop members 27–32 are securely and conventionally attached to an exterior of the lower brace member 21 to prevent rearward movement of the lower portion of the upper brace member 11 relative to the user's knee. Each of the end portions 16,18 of the curved shell 12 of the upper brace member 11 includes a rearwardly curved end 33 which is adapted to limit movement of the upper brace member 11 by coming into contact with respective stop members 27–32. The stop members 27–32 include a first set of the stop members 27–29 which are disposed intermediate of a front and one of the sides of the lower brace member 21 with the first set of the stop members 27–29 being aligned and spaced along a length of the lower brace member 21 and disposed intermediate of the top and a bottom of the lower brace member 21. The stop members 27–32 include a second set of the stop members 30–32 which are disposed intermediate of a front and the other of the sides of the lower brace member 21 with the second set of the stop members 30–32 being aligned and spaced along a length of the lower brace member 21 and disposed intermediate of the top and the bottom of the lower brace member 21. The stop members 27–32 are essentially button-like bearing members which extend outwardly of the curved shell 22 of the lower brace member 21.

In use, the user straps on the lower brace member 21 with the outwardly and forwardly protruding portion 24 of the lower brace member 21 being placed over the user's knee, and the user then straps on the upper brace member 11 about the user's leg above the knee with the roller members 25,26 being movably disposed in the respective tracks 19,20. If the user takes a shot or hit to the front of the knee, the protruding portions 14,24 and the curved ends 33 of the end portions of the upper brace member in cooperation with the stop members 16,18 will prevent the user's knee from hyperextending or being forced rearwardly relative to the leg itself.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A protective knee brace comprising:

an upper brace member having a laterally curved shell and a padded member securely lining a back side of said curved shell, said upper brace member being adapted to fit about a user's leg above and including the knee;

a lower brace member having a laterally curved shell and a padded member securely lining a back side of said curved shell, said lower brace member being adapted to fit about a user leg below and including the knee, said upper brace member having a lower portion which overlaps an upper portion of said lower brace member;

a plurality of fastening members a first ones of which are securely attached to said upper brace member for securing said upper brace member about the user's leg, and second ones of which are securely attached to said lower brace member for securing said lower brace member about the user's leg;

a plurality of tracks disposed in said lower portion of said upper brace member;

a plurality of roller members securely mounted to an exterior of said lower brace member to either side thereof and being adapted to be movably received in said tracks; and a plurality of stop members securely attached to an exterior of said lower brace member to prevent rearward movement of said lower portion of said upper brace member relative to the user's knee.

2. A protective knee brace as described in aim 1, wherein said curved shell of said upper brace member includes a front portion having an outwardly protruding portion near a bottom thereof.

3. A protective knee brace as described in claim 2, wherein said curved shell of said upper brace member includes first and second side portions each of which has an end portion which extends downwardly below said bottom of said front portion thereof.

4. A protective knee brace as described in claim 3, wherein said tracks includes a first one of said tracks which is disposed in and extends along one of said end portions of said curved shell of said upper brace member, and also includes a second one of said tracks which is disposed in and extends along the other of said end portions of said curved shell of said upper brace member.

5. A protective knee brace as described in claim 4, wherein each of said end portions of said curved shell of said upper brace member includes a rearwardly curved end which is adapted to limit movement of said upper brace member by coming into contact with a respective said stop members.

6. A protective knee brace as described in claim 5, wherein said curved shell of said lower brace member includes a front portion having an outwardly protruding portion near a top thereof, said outwardly protruding portion of said lower brace member being adapted to receive the user's knee, said outwardly protruding portion of said upper brace member being adapt to receive said outwardly protruding portion of said lower brace member.

7. A protective knee brace as described in claim 6, wherein said end portions of said side portions of said upper brace member and said outwardly protruding portion of said upper brace member overlap said upper portion of said lower brace member.

8. A protective knee brace as described in claim 7, wherein said roller members are essentially roller bearings which extend outwardly of said lower brace member.

9. A protective knee brace as described in claim 8, wherein said stop members include a first set of said stop members which are disposed intermediate of a front and one of said sides of said lower brace member, said first set of said stop members being aligned and spaced along a length of said lower brace member and disposed intermediate of said top and a bottom of said lower brace member.

10. A protective knee brace as described in claim 9, wherein said stop members include a second set of said stop members which are disposed intermediate of a front and the other of said sides of said lower brace member, said second set of said stop members being aligned and spaced along a length of said lower brace member and disposed intermediate of said top and said bottom of said lower brace member.

11. A protective knee brace as described in claim 10, wherein said stop members are essentially button-like bearing members which extend outwardly of said curved shell of said lower brace member.

12. A protective knee brace as described in claim 11, wherein each of said fastening members includes a strap being securely attached to a respective said brace member and being adapted to wrap about a user's leg, and also includes a buckle also being securely attached to a respective said brace member and being adapted to receive an end portion of a respective said strap.

13. A protective knee brace as described in claim 12, wherein said first ones of said fastening members include a pair of said fastening members being securely attached near a top of said upper brace member.

14. A protective knee brace as described in claim 13, wherein said second ones of said fastening members include a pair of said fastening members being securely attached near said bottom of said lower brace member.

15. A protective knee brace comprising:

an upper brace member having a laterally curved shell and a padded member securely lining a back side of said curved shell, said upper brace member being adapted to fit about a user's leg above and including the knee, said curved shell of said upper brace member including a front portion having an outwardly and forwardly protruding portion near a bottom thereof, said curved shell of said upper brace member including first and second side portions each of which has an end portion which extends downwardly below said bottom of said front portion thereof, said padded member being essentially thinsulate fabric and said curved shell being essentially a high-impact material;

a lower brace member having a laterally curved shell and a padded member securely lining a back side of said curved shell, said lower brace member being adapted to fit about a user leg below and including the knee, said upper brace member having a lower portion which overlaps an upper portion of said lower brace member, said curved shell of said lower brace member including a front portion having an outwardly and forwardly protruding portion near a top thereof, said outwardly and forwardly protruding portion of said lower brace member being adapted to receive the user's knee, said outwardly and forwardly protruding portion of said upper brace member being adapted to receive said outwardly and forwardly protruding portion of said lower brace member, said end portions of said side portions of said upper brace member and said outwardly protruding portion of said upper brace member overlapping said upper portion of said lower brace member, said padded member being essentially a thinsulate fabric and said curved shell being essentially a high-impact material;

a plurality of fastening members a first ones of which are securely attached to said upper brace member for securing said upper brace member about the user's leg, and second ones of which are securely attached to said lower brace member for securing said lower brace member about the user's leg, each of said fastening members including a strap being securely attached to a respective said brace member and being adapted to wrap about a user's leg, and also including a buckle also being securely attached to a respective said brace member and being adapted to receive an end portion of a respective said strap, said first ones of said fastening members including a pair of said fastening members being securely attached near a top of said upper brace member, said second ones of said fastening members including a pair of said fastening members being securely attached near said bottom of said lower brace member;

a plurality of tracks disposed in said lower portion of said upper brace member, said tracks including a first one of said tracks which is disposed in and extends along one of said end portions of said curved shell of said upper brace member, and also including a second one of said tracks which is disposed in and extends along the other of said end portions of said curved shell of said upper brace member;

a plurality of roller members securely mounted to an exterior of said lower brace member to either side thereof and being adapted to be movably received in said tracks, said roller members being essentially roller bearings which extend outwardly of said lower brace member; and a plurality of stop members securely attached to an exterior of said lower brace member to prevent rearward movement of said lower portion of said upper brace member relative to the user's knee, each of said end portions of said curved shell of said upper brace member including a rearwardly curved end which is adapted to limit movement of said upper brace member by coming into contact with a respective said stop members, said stop members including a first set of said stop members which are disposed intermediate of a front and one of said sides of said lower brace member, said first set of said stop members being aligned and spaced along a length of said lower brace member and disposed intermediate of said top and a bottom of said lower brace member, said stop members including a second set of said stop members which are disposed intermediate of a front and the other of said sides of said low brace member, said second set of said stop members being aligned and spaced along a length of said lower brace member and disposed intermediate of said top and said bottom of said lower brace member, said stop members being essentially button-like bearing members which extend outwardly of said curved shell of said lower brace member.

* * * * *